(12) United States Patent
Fabinski et al.

(10) Patent No.: US 6,484,562 B2
(45) Date of Patent: Nov. 26, 2002

(54) GAS ANALYZER AND A METHOD FOR OPERATING THE SAME

(75) Inventors: Walter Fabinski, Kriftel (DE); Peter Schastok, Niederdorfelden (DE); Werner Thies, Bad Camberg (DE)

(73) Assignee: ABB Patent GmbH, Mannheim (DE)

( * ) Notice: Subject to any disclaimer, the term of this patent is extended or adjusted under 35 U.S.C. 154(b) by 0 days.

(21) Appl. No.: 10/085,319

(22) Filed: Feb. 27, 2002

(65) Prior Publication Data

US 2002/0129639 A1 Sep. 19, 2002

Related U.S. Application Data

(62) Division of application No. 09/809,497, filed on Mar. 15, 2001.

(30) Foreign Application Priority Data

Mar. 17, 2001 (DE) .......................................... 100 13 374

(51) Int. Cl.$^7$ ......................... F23J 15/00; G01N 27/46; G01N 21/01; G02B 6/00
(52) U.S. Cl. ...................... 73/31.05; 73/29.31; 73/49.3; 73/864.01; 250/573; 250/339.12
(58) Field of Search ........................... 73/31.05, 864.01, 73/864.81, 31.04, 23.31, 30.03, 40, 49.3; 250/436, 573, 356.1, 339.12

(56) References Cited

U.S. PATENT DOCUMENTS

| | | | | |
|---|---|---|---|---|
| 2,526,038 A | * | 10/1950 | Nelson ........................ 175/183 |
| 2,953,681 A | * | 9/1960 | Frazier ....................... 250/43.5 |
| 4,305,724 A | * | 12/1981 | Micko ....................... 23/232 F |
| 4,392,813 A | * | 7/1983 | Tanaka et al. ................. 431/76 |
| 4,606,219 A | * | 8/1986 | Bout et al. ....................... 73/23 |
| 5,151,252 A | * | 9/1992 | Nass ....................... 422/186.3 |
| 5,315,117 A | * | 5/1994 | Hatton et al. ............. 250/356.1 |
| 5,402,241 A | * | 3/1995 | Jeannotte et al. ........... 356/436 |
| 5,418,615 A | * | 5/1995 | Doyle ........................ 356/436 |
| 5,526,112 A | * | 6/1996 | Sahagen ....................... 356/72 |
| 5,539,386 A | * | 7/1996 | Elliot ........................ 340/632 |
| 5,615,673 A | * | 4/1997 | Berger et al. ................ 128/633 |
| 5,617,077 A | * | 4/1997 | Weimeyer et al. .......... 340/628 |
| 5,658,540 A | * | 8/1997 | Valentino ..................... 423/210 |
| 5,672,887 A | * | 9/1997 | Shaw et al. ................. 250/573 |
| 5,753,797 A | * | 5/1998 | Forster et al. ............. 73/24.01 |
| 6,130,439 A | * | 10/2000 | Le Menn ..................... 250/573 |
| 6,188,813 B1 | * | 2/2001 | Dourdeville et al. .......... 385/12 |
| 6,202,472 B1 | * | 3/2001 | Wezurek et al. ........... 73/31.05 |
| 6,239,445 B1 | * | 5/2001 | Shaeef ........................ 250/576 |
| 6,297,505 B1 | * | 10/2001 | Frandsen et al. ....... 250/339.12 |
| 6,316,781 B1 | * | 11/2001 | Nagle et al. ................. 250/573 |

\* cited by examiner

Primary Examiner—Hezron Williams
Assistant Examiner—David J. Wiggins
(74) Attorney, Agent, or Firm—Michael M. Rickin, Esq.

(57) ABSTRACT

A gas analyzer having an analysis or sensor unit and having an electronic processing unit, and a method for operating such a gas analyzer. In order to achieve substantially improved safety both in handling corrosive and/or combustible and/or toxic gases in a not potentially explosive atmosphere (ex-free atmosphere), and in the operation of such an analyzer in an exatmosphere, the analysis or sensor unit as such is of non-explosive configuration and is arranged in a gas tight chamber through which a toxic and/or corrosive and/or combustible gas flows and around which a second chamber is arranged.

4 Claims, 2 Drawing Sheets

GAS ANALYZER AND A METHOD FOR OPERATING THE SAME

This is a division of application Ser. No. 09/809,497, filed Mar. 15, 2001.

FIELD OF THE INVENTION

This invention relates to a gas analyzer having an analysis or sensor unit and having an electronic processing unit, and to a method for operating such a gas analyzer.

DESCRIPTION OF THE PRIOR ART

Many versions, and also many operating methods, are known for gas analyzers having a sensing unit and an electronic processing unit. In this case, use is made of gas sensors which, depending on configuration, are sensitively set to one or other gases depending on which one is desired for selective measurement. Electronic sensor systems, gel sensors, thermal conduction sensors and other similar sensors are known for this purpose. Solid electrolyte sensors are also known, in particular for oxygen analysis.

Also known, however, over and above this are optical gas analysis methods in the case of which a cuvette flowed through by measuring gas is transradiated starting from a light source of specific radiation bands. Arranged on the side of the cuvette opposite the light source is a detector which picks up a measurement signal based on an optopneumatic effect. The detector is sensitively set to the measuring gas component to be measured, and measures the residual signal remaining in terms of absorption after passage through the cuvette. This is inversely proportional to the partial pressure fraction of the measuring gas component in the measured gas sample. Because of this inversely proportional relationship, so-called absorption spectroscopy is also involved here. Such methods are generally used as absorption photometers with appropriate light sources.

In the case of use in process measurement techniques, that is to say in online measurement of industrial process cycles, for the most part gas samples are taken which are sent via the analyzer. Explosion protection precautions are to be taken for the eventuality that the gases are toxic or combustible.

In chemical process engineering, however, it is frequently necessary to solve measurement tasks in which one or more gas components in corrosive and/or toxic and/or combustible gases are to be analyzed. As a rule, the extractive measurement techniques currently on offer have special properties in order to meet the requirements of measurement techniques and safety. For this purpose, expensive use is made of specialists who are employed in potentially explosive atmospheres (ex-atmospheres) and also in corrosive and toxic gases together with housing purging (pressurized enclosure) and a pressure tight enclosure, that are to be monitored. It frequently happens that some damage has already occurred before the service staff can intervene.

It is therefore the object of the invention to improve a gas analyzer and a method for operating such in order substantially to improve safety both in handling corrosive and/or combustible and/or toxic gases in a not potentially explosive atmosphere (ex-free atmosphere) and in the operation of such an analyzer in an ex-atmosphere.

SUMMARY OF THE INVENTION

The solution according to the invention takes account in this case both for the gas analyzer and for the operating method both in the first case in which combustible gases are to be analysed in the ex-free atmosphere, and of the second case, in which the combustible gas is present in an ex-atmosphere. In the second-named case, it is necessary to add appropriate configurations, as described below.

Likewise to be distinguished are the gas analyzer groups already described at the beginning in the prior art. These are, firstly, the group of optical gas analyzers and also others such as the group of thermal conduction sensors and solid electrolyte or gel sensors.

The second-named case corresponds in essence to a gas analyzer in accordance with Claim 1. The core of the invention there consists in that in the case of the analysis of a toxic and/or corrosive and/or combustible gas the analysis or sensor unit as such is of nonexplosive (for example intrinsically safe) configuration and is arranged in a gastight chamber around which a second chamber is arranged. This case is that of a gas analyzer with an integrated sensor unit and integrated processing unit.

However, these are arranged in a common housing in separate parts of the same. The sensor region arranged inside the housing is correspondingly provided with a non-combustible sensor which is arranged in a first chamber, the second chamber then being arranged around this first chamber and thus being placed between a first chamber, containing the sensor, and the remaining space, in which the electronic system is arranged. This yields an appropriately ex-protected separation between the sensor chamber and electronic system. If toxic or combustible or corrosive gases are then fed to the sensor, they remain basically inside the first chamber, which contains the sensor. For safety purposes, the second chamber, which is arranged around the first chamber, shields the latter in turn.

It is provided in an appropriate refinement in the case of this variant apparatus that the second chamber is purged with an inert gas or with air. If a leak were to occur in this case through the first chamber, toxic or corrosive or combustible measuring gas would flow via this leakage only into the second chamber, which is, in turn, purged permanently by an inert gas. The effect, in turn, is to dispose of the leakage gas into a closed purging gas system, the leakage gas thereby being simultaneously substantially thinned by the purging. Consequently, in the way provided by the invention, not only is leakage counteracted, but leakage and/or the dangerous gas emerging because of the leakage can be diluted until it is unobjectionable, and thereby be branded safe.

In a second independent device claim, the correspondingly identical methodology is applied to an analyzer which is based on an optical detection method such as, for example, on absorption photometry. In this case, the element of corresponding consideration is the cuvette. The cuvette contains a measuring gas inlet and a measuring gas outlet. That is to say there is no gas contact with the detector as such, and the cuvette remains a closed system. In order now to fulfill the ex-protection preconditions in the way according to the invention, the said cuvette is surrounded either partially or completely by a second space.

A purging gas is fed inside this second space or the second chamber, if the cuvette is defined as a first chamber, and appropriately discharged again. The purging gas used must fulfill two preconditions in this case. Firstly, the purging gas must be inert or have at least essentially such properties, and, secondly, it is not permitted to effect any appreciable absorption of that radiation band which is directed sensitively to the measuring gas. The general absorption which occurs through the plurality of the windows now occurring can be taken into account by prior gauging or by calibration. Of course, it is also possible, going beyond this, also to take account of absorptive purging gas as well by appropriate calibration.

The same holds for the case of leakage and for the ex-protection as such as did for the first-named embodiment. If a leakage occurs in the critical region leading the toxic or corrosive or combustible measuring gas, specifically in the cuvette, the leakage gas enters only the second space, which surrounds the measuring cuvette. Since this space or this chamber is, in addition, permanently purged by means of purging gas, as in the first example there is a steady thinning of the critical gas. Likewise, the critical gas is led out of the system, and possibly out of the ex-atmosphere.

As already mentioned, it holds for both variants that the second chamber is purged with inert gas or with air.

Furthermore, according to the invention it is advantageously provided both for the first and for the second variant that a pressure higher by comparison with the first chamber is set in the second chamber. This also produces a delimitation in terms of gas dynamics by comparison with gas possibly escaping from the first chamber.

Furthermore, it is advantageously provided both for the first and for the second variant that a flow sensor is used for monitoring the purging gas. The purging gas flow can be monitored by means of this sensor and sensitive warning sensors which, as the case may be, are connected downstream can detect critical gas compositions which can, in turn, have a regulating effect on the purging gas flow.

Both examples named so far relate essentially to the use of a combustible (possibly an explosive) gas in the ex-free atmosphere. That is to say, the ex-atmosphere exists only inside the analyzer, and is kept away from the electric systems with the aid of appropriate measures.

However, a second field of use is yielded by use in the so-called ex-atmosphere. In order to render such devices capable of this, as well, the devices as such are additionally protected overall in the outer region by secondary ex-protective measures (for example pressurizing enclosure, pressuretight enclosure).

However, it is important to note in this case that the invention is essentially directed firstly to the use of toxic or corrosive or combustible gases, which are fed to the analyzer, initially independently of whether the environment is in the potentially explosive atmosphere or the not potentially explosive atmosphere. The second-mentioned case concerns the handling of toxic or corrosive or combustible gases inside the analyzer, in which case the latter is also arranged, in turn, in an ex-atmosphere.

With reference to a method for operating such a gas analyzer, it is provided according to the invention that in the case of analysis of a toxic or corrosive or combustible gas a space arranged around the analysis or sensor unit is flowed around or through by a purging gas, an overpressure being set in the purged space by comparison with the analysis gas space. Consequently, for safety reasons, appropriate pressure gradients are set up which reliably prevent leakage gas from escaping into the purging gas path and thus into the environment.

It is advantageously provided, furthermore, that purging is performed via a regulator by virtue of the fact that fractions of toxic or corrosive or combustible gas components in the purging gas can be detected by a sensor and, thereupon, the throughput of purging gas can be increased under regulation.

It is advantageously provided, furthermore, that a change in the purging gas flow or in the pressure is recorded in the test record for later correction, if appropriate.

It is possible thereby to achieve an influence which is to be corrected accordingly, in particular in the case of optical gas analysis methods. It is possible to detect at least in which time phase the measurement results are possibly unreliable.

In a further advantageous embodiment, it is specified that the entire system is caused to shut down in the event of the detection of an escaping gas.

In a last advantageous refinement, it is provided that underpressure purging can also be performed. That is to say, in this case the pressure of the purging gas in the second chamber is lower than the pressure in the first chamber, which leads the measuring gas. This results at the same time in purging and, correspondingly, extraction.

DESCRIPTION OF THE PREFERRED EMBODIMENT(S)

Figure 1:
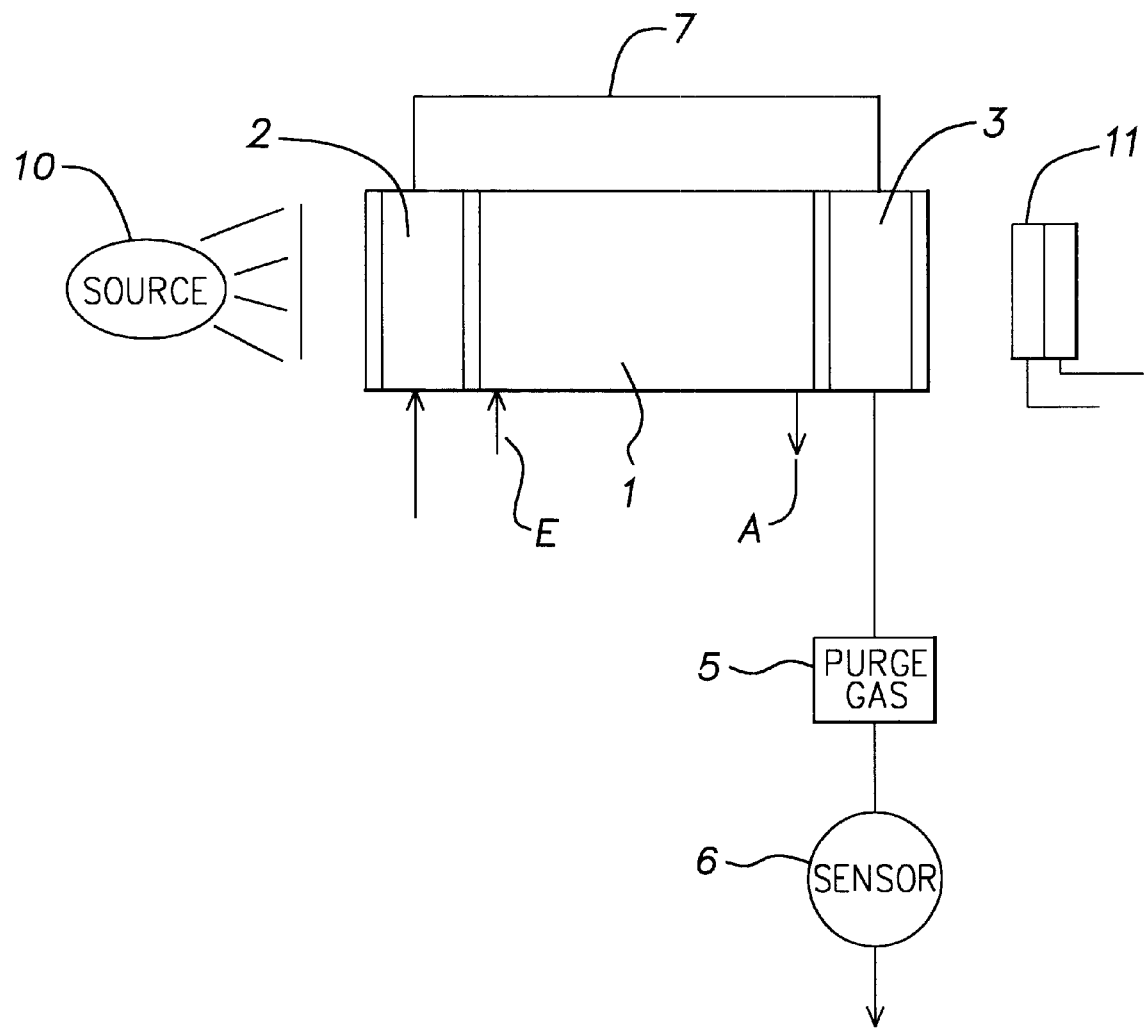
FIG. 1 shows a design according to the invention with a cuvette.

FIG. 1 shows the use of the invention in terms of apparatus in the case of absorption photometry, by way of example. In this case, the system purged by the measuring gas is the measuring cuvette 1 as such. The latter comprises a tubular element having a measuring gas input E and a measuring gas output A. The entry window for the radiation from a radiation source 10 is in the region of the inlet E, and the outlet window for the radiation passing the cuvette is in the region of the measuring gas exit A, said radiation then being led to the detector 11.

Overall, the cuvette 1 is surrounded respectively by a second chamber 2, 3, at least in the region of the entry and outlet windows. Since otherwise the cuvette comprises a closed metallic tube, leakages can occur only at the built-in windows. Consequently, a purging chamber can be provided only upstream of the entry window, and a purging chamber can be provided upstream of the exit window. In this case the two component chambers 2, 3 are connected at the entry window and at the exit window to a gas line 7 such that the two component chambers 2, 3 can be flowed through serially by the purging gas. However, for the purpose of enhanced protection of the system, the entire cuvette can also be provided on the outside with a closed second chamber to which purging gas is applied, or through which purging gas is passed, as appropriate. In this case, a leakage in the cuvette region leads only to the critical gas escaping into the purging chamber.

A purging gas monitoring unit 5 having a sensor 6 and built into the purging system monitors whether leakage gas occurs. If this happens, the purging or the purging throughput can be increased. This holds, in particular, for the case of overpressure purging in which the pressure in the purging chamber region is higher than in the cuvette region. However, it is also possible to purge using underpressure, in which case the purging gas pressure is lower than the gas pressure in the cuvette. In the second-named case, the detection of a leakage gas in the purging system can lead to a further throughput, which can also lead to a lowering or to a further lowering in the pressure in the purging system.

Figure 2:
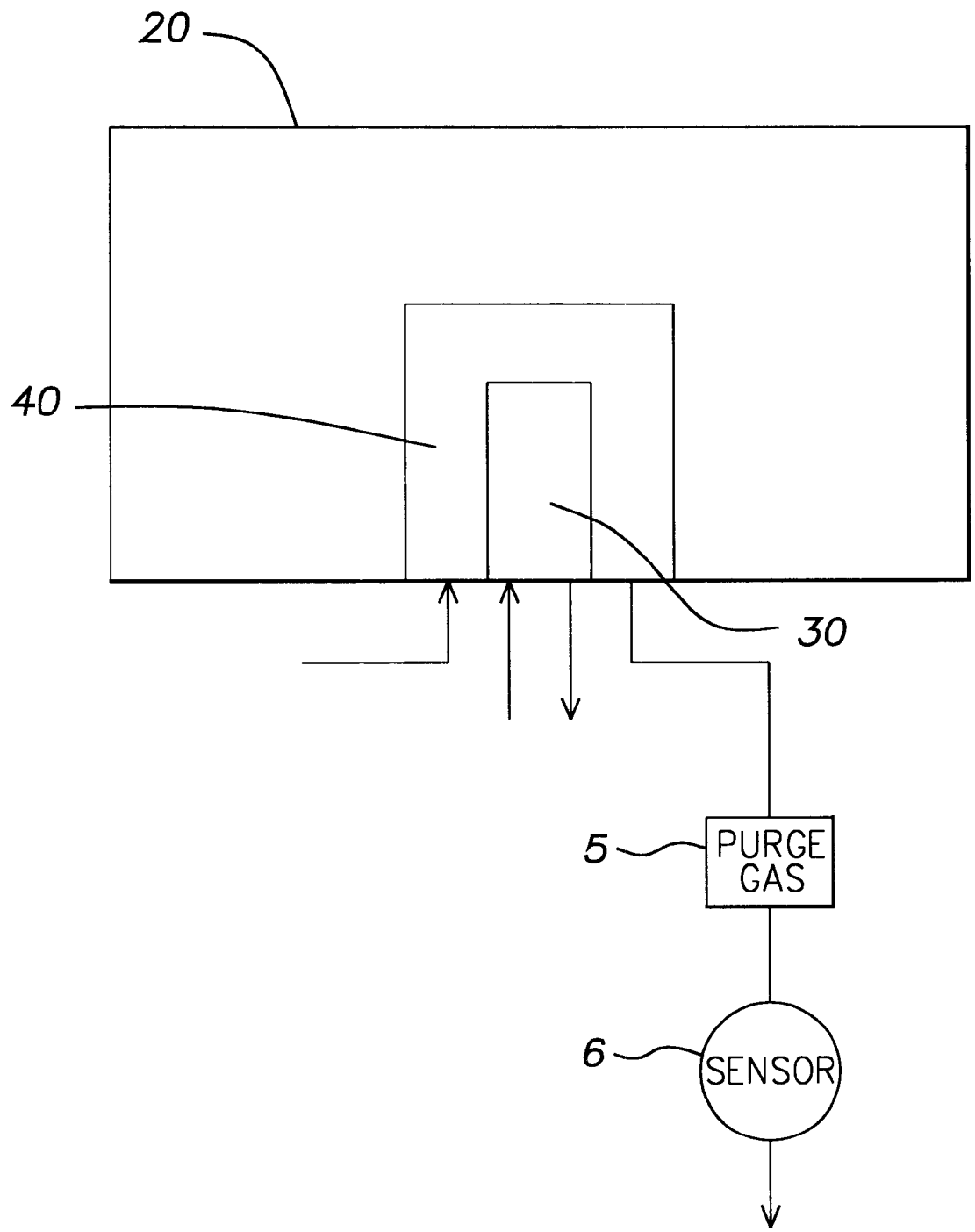
FIG. 2 shows an embodiment according to the invention with a sensor.

FIG. 2 shows a gas analyzer having a sensor unit and a processing unit in a housing 20. A non-explosive (for example intrinsically safe) sensor is arranged in a first sensor chamber 30 for the case in which only combustible gas is used. The toxic or corrosive or combustible measuring gas is introduced into this sensor chamber 30 and extracted therefrom. The sensor chamber 30 is surrounded in the way according to the invention by a second chamber 40 which can optionally be purged. This second chamber 40 is a hermetic space between the sensor 30 chamber 30 and the housing 20 containing the electronic system. The escape of corrosive or toxic or combustible gas towards the analyzer is thereby prevented. The purging gas system operates in the same way as already mentioned in the above-named example.

For the purpose of using the two analyzers in accordance with FIG. 1 and FIG. 2 in a potentially explosive atmosphere, the system can be further protected by secondary ex-protective measures (for example pressurizing enclosure, pressuretight enclosure). It is possible overall to provide an emergency shutdown unit which, upon leakage of the measuring gas, shuts down the entire system.

It is to be understood that the description of the preferred embodiment(s) is (are) intended to be only illustrative, rather than exhaustive, of the present invention. Those of ordinary skill will be able to make certain additions, deletions, and/or modifications to the embodiment(s) of the disclosed subject matter without departing from the spirit of the invention or its scope, as defined by the appended claims.

What is claimed is:

1. A gas analyzer of the type that uses the principle of optical gas analysis comprising:

an appropriate cuvette flowed through by a gas to be measured, said flowing gas providing a measuring pressure in said cuvette; said cuvette having a window region placed near an analysis space and said cuvette surrounded either only in said window region or overall by a chamber that isolates any leakage from said measuring cuvette when said gas analyzer is analyzing a toxic and/or corrosive and/or combustible gas that flows thru said analysis space said surrounding chamber is purged with inert gas or air and having a pressure higher or lower by comparison with said measuring pressure of said cuvette.

2. The gas analyzer of claim 1 further comprising a flow sensor for monitoring flow of said inert gas or air to regulate said inert gas or air flow.

3. The gas analyzer of claim 1 further comprising a processing unit.

4. The gas analyzer of claim 3 wherein said processing unit is an electronic unit.

* * * * *